US00PP22628P3

(12) United States Plant Patent
Kristensen

(10) Patent No.: US PP22,628 P3
(45) Date of Patent: Apr. 3, 2012

(54) ***OSTEOSPERMUM* PLANT NAMED 'SAKOST8077'**

(50) Latin Name: *Osteospermum hybrida*
Varietal Denomination: SAKOST8077

(75) Inventor: Niels G. Kristensen, Silkeborg (DK)

(73) Assignee: Sakata Ornamentals Europe A/S, Marslev (DK)

( * ) Notice: Subject to any disclaimer, the term of this patent is extended or adjusted under 35 U.S.C. 154(b) by 204 days.

(21) Appl. No.: 12/657,835

(22) Filed: Jan. 28, 2010

(65) Prior Publication Data

US 2011/0185461 P1 Jul. 28, 2011

(51) Int. Cl.
*A01H 5/00* (2006.01)

(52) U.S. Cl. ..... Plt./360

(58) Field of Classification Search ..... Plt./360
See application file for complete search history.

(56) References Cited

U.S. PATENT DOCUMENTS

PP18,112 P2 * 10/2007 Dummen ..... Plt./360

(Continued)

OTHER PUBLICATIONS

UPOV ROM GTITM Computer Database, GTI Jouve Retrieval Software 2011/01 Citation for 'SAKOST8077'.*

*Primary Examiner* — Wendy C Haas
(74) *Attorney, Agent, or Firm* — Jondle & Associates, P.C.

(57) ABSTRACT

A new *Osteospermum* plant particularly distinguished by having medium-sized, terracotta-colored flowers with greyed-purple centers (disc florets), oval-shaped leaves, and semi-erect plant habit, is disclosed.

1 Drawing Sheet

U.S. PATENT DOCUMENTS

PP20,522 P2 * 12/2009 Kristensen ..... Plt./360

* cited by examiner

Genus and species: *Osteospermum hybrida.*
Variety denomination: 'SAKOST8077'.

BACKGROUND OF THE NEW PLANT

The present invention comprises a new and distinct cultivar of *Osteospermum,* botanically known as *Osteospermum hybrida,* and hereinafter referred to by the cultivar name 'SAKOST8077'. 'SAKOST8077' originated from a hybridization of unpatented proprietary hybrid *Osteospermum* lines '203149' and '204059' in Aabyhoej, Denmark. The female parent, '203149', has a light yellow and white flower color with a purple ring and blue eye zone. The male parent, '204059', has a copper-purple flower color.

In May 2005, the two *Osteospermum* lines were crossed and seeds were obtained. The seeds were sown and 300 $F_1$ plants were grown in pots for evaluation. A single plant having medium-sized terracotta-colored flowers with greyed-purple centers (disc florets) was selected for further evaluation and propagation.

In February 2006, the single plant was vegetatively propagated by cuttings and re-evaluated in an open field and a greenhouse, and assigned the breeder code number '206101'.

In spring 2006, '206101' plants were evaluated again in pots and in an open field. '206101' was named 'SAKOST8077' and was found to reproduce true to type in successive generations of asexual propagation through vegetative cuttings.

SUMMARY OF THE INVENTION

The following are the most outstanding and distinguishing characteristics of this new cultivar when grown under normal horticultural practices in Salinas, Calif.

1. Terracotta-colored flowers with greyed-purple centers (disc florets);
2. Medium flower size;
3. Oval shaped leaves; and
4. Semi-erect plant habit.

DESCRIPTION OF PHOTOGRAPHS

This new *Osteospermum* plant is illustrated by the accompanying photographs which show the plant's overall plant habit including form, foliage, and flowers. The photographs are of a plant grown six months from transplant date and ten months from stick date into 8-inch pots from rooted cuttings in Salinas, Calif. in the spring of 2009 through the winter of 2010. The colors shown are as true as can be reasonably obtained by conventional photographic procedures.

DESCRIPTION OF THE NEW CULTIVAR

Figure 1:
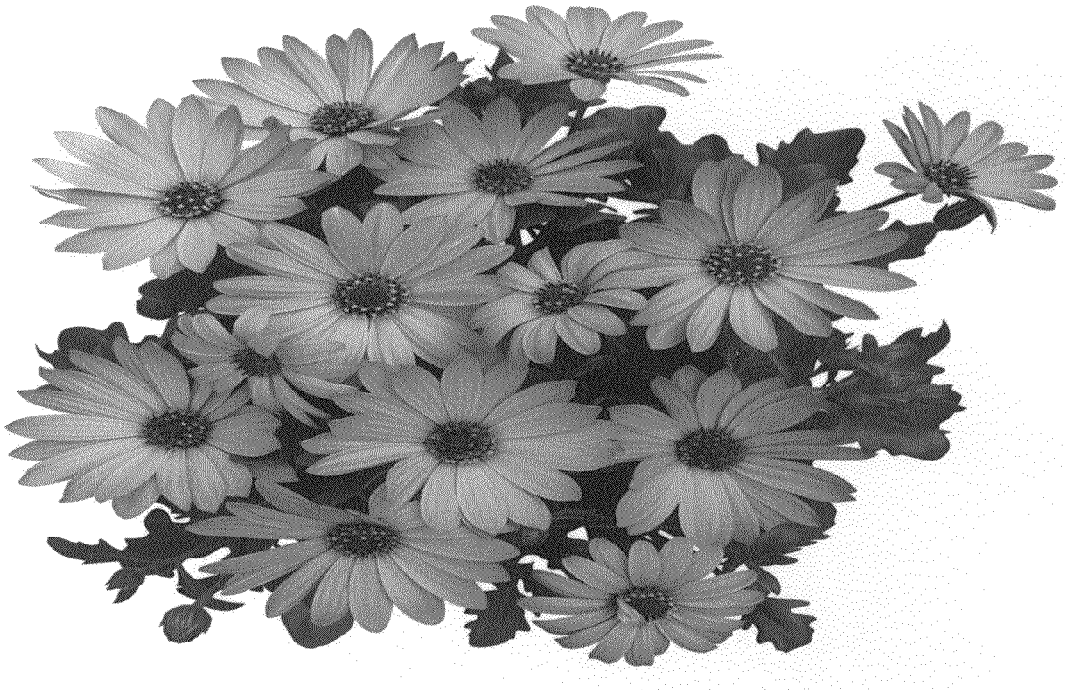
FIG. 1 shows overall plant habit of the plant grown in a pot.
Figure 2:
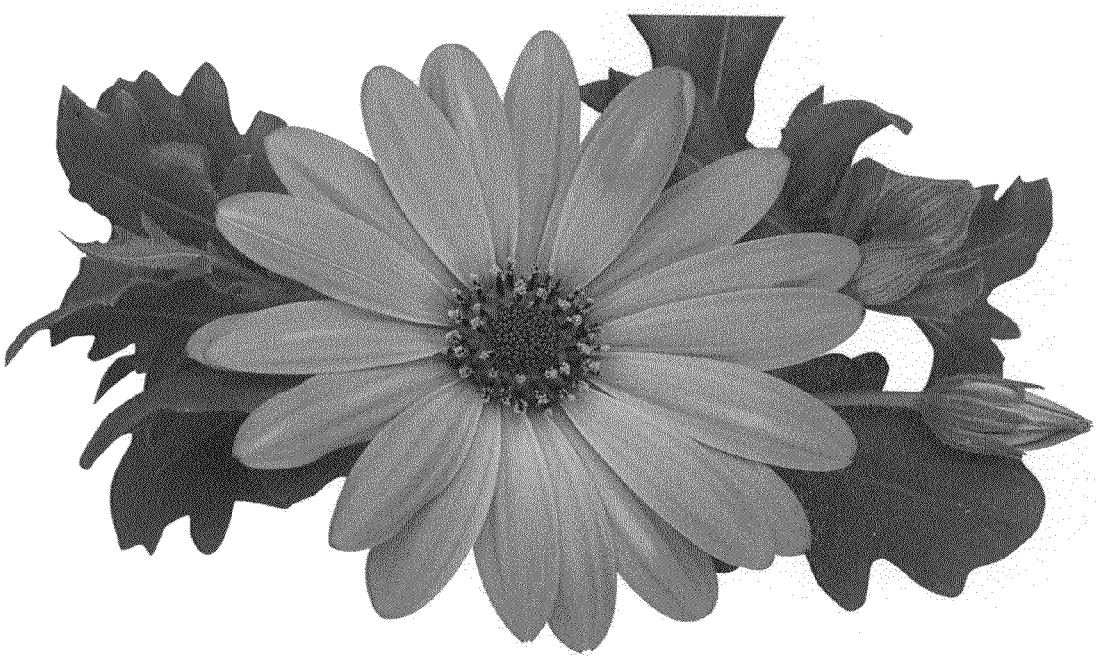
FIG. 2 shows the mature inflorescence of the plant.

The following detailed descriptions set forth the distinctive characteristics of 'SAKOST8077'. The data which define these characteristics were collected from asexual reproductions carried out in Salinas, Calif. Data was collected on plants grown approximately six months from transplant date and ten months from stick date into 8-inch pots under greenhouse conditions in Salinas, Calif. in the spring of 2009 through the winter of 2010. Color references are to The R.H.S. Colour Chart of The Royal Horticultural Society of London (R.H.S.), $4^{th}$ edition.

DESCRIPTION OF THE NEW PLANT

Classification:
*Family.*—Compositae.
*Botanical.*—*Osteospermum hybrida.*
*Common.*—*Osteospermum,* Cape Daisy, South African Daisy.
*Designation.*—'SAKOST8077'.

Parentage:
*Female parent.*—A hybrid proprietary *Osteospermum* line '203149' (unpatented).
*Male parent.*—A hybrid proprietary *Osteospermum* line '204059' (unpatented).

Growth:
*Time to produce a rooted cutting.*—Cuttings will colonize a 2.5 cm diameter by 2.5 cm tall greenhouse tray cell with peat-based plant media in approximately four weeks. Cuttings are dipped in a normal dilution (1:9) of DIP 'N GROW root inducing solution in water. The trays are misted hourly during rooting.
*Environmental conditions for plant growth.*—Rooted cuttings are transplanted to pots with a 16 cm diameter, one plant per pot. Peat-based growing media is used. The pots are watered using a 150 ppm to 200 ppm fertilizer solution using 18-8-18 fertilizer. The soil is allowed to dry between watering. During the first few weeks after transplanting, the plants should have evening temperatures around 15° C. to 18° C. for good root growth. When plants reach 7.5 cm to 10 cm in height, they are pinched back to 5 to 6 leaves to promote branching. Spring and summer daytime high temperatures in Salinas, Calif., where the data was collected, range from 16° C. to 25° C.
*Time to bloom from propagation.*—Approximately four weeks when rooted vegetative cuttings are transferred to a 5-inch diameter pot. Flowering season is all year in the United States. Vernalization is not required to induce flowering.

Plant Description:
*Habit.*—Semi-erect.
*Life cycle.*—Perennial.
*Form.*—Semi-erect.
*Height* (*from soil line to first node*).—2.0 cm.
*Height* (*from soil line to top of foliage*).—28.0 cm to 30.0 cm.
*Width.*—48.0 cm to 50.0 cm.

Stems:
*General.*—Multiple stems, circular in cross section.
*Stem length* (*total*).—15.0 cm to 16.0 cm.
*Diameter.*—0.2 cm.
*Internode length.*—2.0 cm.
*Color.*—RHS 143B (Green).
*Pubescence.*—Moderate. Color: RHS N155A (White). Shape: Short, hair-like fibers.

Branches:
*General.*—Circular in cross section.
*Number of main branches.*—1.
*Total number of branches.*—20.
*Length.*—14.0 cm to 15.0 cm, approximately 2.0 cm from soil line to first node, 2.0 cm between first and second nodes.
*Diameter.*—0.6 cm.
*Internode length.*—2.0 cm.
*Color.*—RHS 143A (Green).
*Pubescence.*—Moderate. Color: RHS N155A (White). Shape: Short, hair-like fibers.

Leaves:
*Arrangement.*—Alternate.
*Shape.*—Oval, toothed.
*Apex.*—Acute.
*Base.*—Attenuate.
*Margin.*—Serrate.
*Venation.*—Pinnate.
*Surface* (*both surfaces*).—Dull.
*Surface pubescence* (*both surfaces*).—Very slight, mainly around edge.
*Pubescence color* (*both surfaces*).—RHS N155A (White).
*Attachment.*—Decurrent.
*Length.*—6.0 cm.
*Width.*—3.0 cm.
*Thickness.*—Less than 0.1 cm.
*Color.*—Upper surface: RHS 137A (Green). Lower surface: RHS 137B (Green).
*Venation color.*—Upper surface: RHS 144A (Yellow-green). Lower surface: RHS 144B (Yellow-green).

Inflorescence:
*Number per plant.*—26.
*Type.*—Capitulum (head); disc florets are perfect and ray florets are carpellate.
*Flowering habit.*—Determinate.
*Lastingness of flowers.*—3 to 4 days.
*Fragrance.*—Absent.
*Seed production.*—None observed.
*Diameter.*—6.0 cm.
*Depth.*—1.0 cm.
*Petal* (*ray floret*) *number.*—20 to 22 per inflorescence.
*Disc diameter.*—1.2 cm.
*Disc floret number.*—60 to 80 per inflorescence.
*Peduncle length.*—6.0 cm from inflorescence to first node.
*Peduncle diameter.*—0.2 cm.
*Peduncle color.*—RHS 143B (Green).
*Peduncle texture.*—Dull, slight pubescence.
*Phyllaries.*—Arrangement: 18 per inflorescence, free, arranged symmetrically. Length: 1.0 cm. Width: 0.1 cm. Apex: Acute. Margin: Entire. Shape: Linear, acute. Color: Upper surface: RHS 143A (Green). Lower surface: RHS 143B (Green).

Ray florets (Ligules):
*Corolla.*—One petal per ray floret; only the outer row of florets are the ray florets.
*Number of ray florets.*—20 to 22 per inflorescence.
*Length.*—2.8 cm.
*Width.*—0.6 cm.
*Shape.*—Lanceolate.
*Apex.*—Acute.
*Margin: Entire.*
*Color.*—Upper surface: RHS 26A (Orange). Lower surface: RHS 26B (Orange).
*Pubescence.*—Glabrous.

Disc florets:
*Color.*—RHS 183A (Greyed-purple).
*Shape.*—Tubular.
*Apex.*—Pointed.
*Surface.*—Dull, pubescent.
*Size.*—Length: 0.4 cm. Width: 0.1 cm.

Reproductive organs:

*Ovary.*—Superior in ray florets.

*Pistil form.*—One style with two stigma branches in ray florets.

*Pistil length.*—0.5 cm in ray florets.

*Stigma color.*—RHS 187A (Greyed-purple) in ray florets.

*Style color.*—RHS 155A (White) in ray florets.

*Ovary.*—Superior in disc florets.

*Pistil form.*—One style with two stigma branches in disc florets.

*Stamens.*—5, fused into a single tube in disc florets.

*Anther color.*—RHS 187A (Greyed-purple) in disc florets.

*Pollen color.*—RHS 17A (Yellow-orange) in disc florets.

*Filament color.*—RHS 155A (White) in disc florets.

Disease and insect resistance: Has not been tested for resistance to diseases. However, plants are susceptible to aphids, thrips, whiteflies, and worms.

COMPARISON WITH PARENTAL LINES AND KNOWN CULTIVAR

'SAKOST8077' is a distinct variety of *Osteospermum* owing to its medium-sized, terracotta-colored flowers with brown centers (disc florets), oval-shaped leaves, and semi-erect plant habit. 'SAKOST8077' is distinguished from its parents as described in Table 1 (color references are to The Royal Horticultural Society Colour Chart, 4$^{th}$ edition):

TABLE 1

Comparison with Parental Lines

| Characteristic | 'SAKOST8077' | Male Parent '204059' | Female Parent '203149' |
|---|---|---|---|
| Ray floret (ligule) color, upper surface | RHS 26A (Orange) | Copper-purple | Light yellow and white flowers with a purple ring and blue eye zone |

'SAKOST8077' is a distinct variety of *Osteospermum* owing to its medium-sized, terracotta-colored flowers with brown centers (disc florets), oval-shaped leaves, and semi-erect plant habit. 'SAKOST8077' is most similar to the *Osteospermum* plant named 'SAKOST3586' (U.S. Plant Pat. No. 20,522). Differences between the two varieties are described in Table 2 (color references are to The Royal Horticultural Society Colour Chart, 4$^{th}$ edition):

TABLE 2

Comparison with Similar Variety

| Characteristic | 'SAKOST8077' | 'SAKOST3586' |
|---|---|---|
| Ray floret (ligule) color, upper surface | RHS 26A (Orange) | RHS 18A (Yellow-orange) at tip, RHS N78B (Purple) at the base with streaks of RHS N78C (Purple) from base to tip, with the color fading closer to the tip |
| Disc floret color | Greyed-purple | Yellow-grey/green |
| Leaf shape | Oval, serrated | Oblanceolate, serrated |

I claim:

1. A new and distinct cultivar of *Osteospermum* plant as shown and described herein.

* * * * *